(12) United States Patent
Burnett et al.

(10) Patent No.: US 9,895,183 B2
(45) Date of Patent: *Feb. 20, 2018

(54) LINER FOR CRYOGENIC TREATMENT SYSTEMS

(71) Applicant: Channel Medsystems, Inc., Emeryville, CA (US)

(72) Inventors: Daniel R. Burnett, San Francisco, CA (US); William Malecki, Piedmont, CA (US)

(73) Assignee: Channel Medsystems, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/029,641

(22) Filed: Sep. 17, 2013

(65) Prior Publication Data

US 2015/0080869 A1  Mar. 19, 2015

(51) Int. Cl.
*A61B 18/02* (2006.01)
*A61B 18/00* (2006.01)
*A61B 17/42* (2006.01)

(52) U.S. Cl.
CPC ...... *A61B 18/02* (2013.01); *A61B 2017/4216* (2013.01); *A61B 2018/00559* (2013.01); *A61B 2018/00577* (2013.01); *A61B 2018/0212* (2013.01)

(58) Field of Classification Search
CPC ............. A61B 2018/0022–2018/00267; A61B 2018/00559; A61B 2018/00577; A61B 2018/0212; A61B 2018/0262; A61B 18/02
USPC ..................................................... 606/20–26
See application file for complete search history.

(56) References Cited

U.S. PATENT DOCUMENTS

| | | |
|---|---|---|
| 2,849,002 A | 8/1958 | Oddo |
| 3,924,628 A | 12/1975 | Droegemueller |
| 4,949,718 A | 8/1990 | Neuwirth |
| 5,084,044 A | 1/1992 | Quint |

(Continued)

FOREIGN PATENT DOCUMENTS

| | | |
|---|---|---|
| WO | WO 2010/135602 | 11/2010 |
| WO | WO 2012/106260 | 8/2012 |

OTHER PUBLICATIONS

International Patent Application No. PCT/US2012/023176 filed Dec. 19, 2003 in the name of Channel Medsystems, Inc., International Search Report and Written Opinion dated Jun. 21, 2012.

(Continued)

*Primary Examiner* — Daniel Fowler
(74) *Attorney, Agent, or Firm* — Levine Bagade Han LLP

(57) ABSTRACT

Liners for cryogenic treatment systems are described where a cryogenic fluid or gas may be introduced into a liner expanded within a body lumen such as the uterine cavity. The liner may be intentionally sized to be substantially larger than the typical size of the uterine cavity, e.g., 1.2 times (or more), greater than the size of the uterine cavity into which the liner is inserted. Because the liner is sized intentionally larger than the body lumen to be treated, the liner may never fully expand when deployed. But even with folds or portions of the liner being folded upon itself, the liner may remain sufficiently supple such that the resulting uncontrolled folds allow for complete conformance of the liner against the anatomy of the contacted tissue.

6 Claims, 6 Drawing Sheets

(56) References Cited

U.S. PATENT DOCUMENTS

| | | | |
|---|---|---|---|
| 5,334,181 A | 8/1994 | Rubinsky et al. | |
| 5,501,681 A | 3/1996 | Neuwirth et al. | |
| 5,730,756 A * | 3/1998 | Kieturakis | A61B 17/0218 128/898 |
| 5,865,801 A * | 2/1999 | Houser | 604/103.07 |
| 5,879,347 A | 3/1999 | Saadat | |
| 6,066,132 A * | 5/2000 | Chen et al. | 606/28 |
| 6,159,160 A | 12/2000 | Hsei et al. | |
| 6,270,476 B1 | 8/2001 | Santoianni et al. | |
| 6,270,493 B1 | 8/2001 | Lalonde et al. | |
| 6,280,439 B1 | 8/2001 | Martin et al. | |
| 6,283,959 B1 | 9/2001 | Lalonde et al. | |
| 6,355,029 B1 * | 3/2002 | Joye et al. | 606/21 |
| 6,554,780 B1 | 4/2003 | Sampson et al. | |
| 6,569,158 B1 | 5/2003 | Abboud et al. | |
| 6,575,932 B1 | 6/2003 | O'brien et al. | |
| 6,648,879 B2 | 11/2003 | Joye et al. | |
| 6,743,184 B2 | 6/2004 | Sampson et al. | |
| 6,752,802 B1 | 6/2004 | Isenberg | |
| 6,872,183 B2 | 3/2005 | Sampson et al. | |
| 6,875,209 B2 | 4/2005 | Zvuloni et al. | |
| 6,951,569 B2 | 10/2005 | Nohilly | |
| 7,063,670 B2 | 6/2006 | Sampson et al. | |
| 7,101,367 B2 | 9/2006 | Xiao et al. | |
| 7,381,208 B2 | 6/2008 | van der Walt et al. | |
| 7,500,973 B2 | 3/2009 | Vancelette et al. | |
| 7,566,341 B2 | 7/2009 | Keller et al. | |
| 7,727,228 B2 | 6/2010 | Abboud | |
| 7,794,454 B2 | 9/2010 | Abboud et al. | |
| 8,206,345 B2 | 6/2012 | Abboud et al. | |
| 8,225,643 B2 | 7/2012 | Abboud | |
| 8,382,747 B2 | 2/2013 | Abboud et al. | |
| 9,027,389 B2 | 5/2015 | Abboud et al. | |
| 2002/0045893 A1 * | 4/2002 | Lane et al. | 606/21 |
| 2002/0087208 A1 * | 7/2002 | Koblish et al. | 607/113 |
| 2002/0095148 A1 * | 7/2002 | Kinsella et al. | 606/41 |
| 2002/0099364 A1 * | 7/2002 | Lalonde | 606/21 |
| 2002/0198578 A1 * | 12/2002 | Dobak, III | 607/104 |
| 2005/0107855 A1 | 5/2005 | Lennox et al. | |
| 2007/0088247 A1 | 4/2007 | Bliweis et al. | |
| 2007/0203396 A1 | 8/2007 | Mccutcheon et al. | |
| 2007/0237739 A1 | 10/2007 | Doty | |
| 2008/0281317 A1 | 11/2008 | Gobel | |
| 2009/0076573 A1 | 3/2009 | Burnett et al. | |
| 2009/0138000 A1 | 5/2009 | Vancelette et al. | |
| 2009/0306588 A1 | 12/2009 | Nguyen et al. | |
| 2011/0082489 A1 | 4/2011 | Davies, Jr. et al. | |
| 2011/0152722 A1 | 6/2011 | Yackel | |
| 2012/0197245 A1 * | 8/2012 | Burnett et al. | 606/21 |
| 2013/0110066 A1 | 5/2013 | Sharma et al. | |
| 2014/0012156 A1 | 1/2014 | Burnett et al. | |

OTHER PUBLICATIONS

Lewis, Richard B. et al., A Method for Determining Contour Volume of the Uterine Cavity, Contraception, Oct. 1970, pp. 249-257, vol. 2, No. 4, Department, Department of Obstetrics and Gynecology, Chicago, Illinois.

* cited by examiner

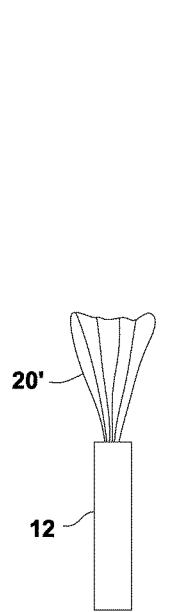 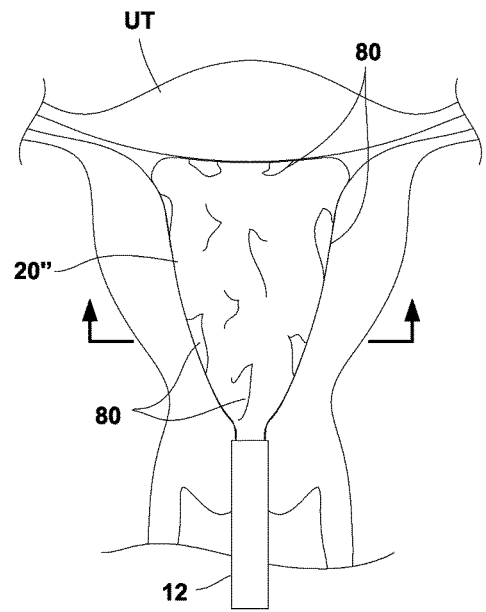 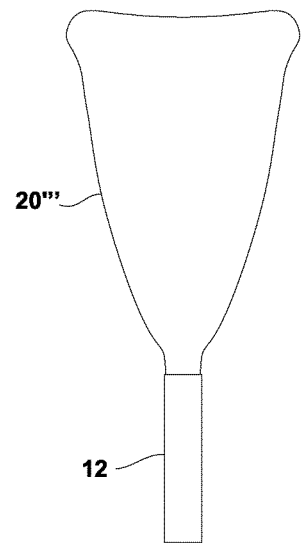
FIG. 5A  FIG. 5B  FIG. 5C
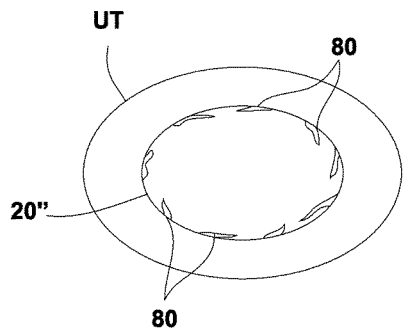
FIG. 5D

LINER FOR CRYOGENIC TREATMENT SYSTEMS

FIELD OF THE INVENTION

The present invention relates to medical devices. In particular, the present invention relates to methods and apparatus for liners which are used in therapeutic devices for cryoablating tissue in bodies with variable anatomy.

BACKGROUND OF THE INVENTION

In the last few decades, therapeutic intervention within a body cavity or lumen has developed rapidly with respect to delivery of energy via radiofrequency ablation. While successful in several arenas, radiofrequency ablation has several major downsides, including incomplete ablation, frequent lack of visualization during catheter insertion, potential for overlap during treatment (with some areas receiving twice as much energy as other areas), charring of tissues and requirements for frequent debridement, frequent requirements for additional doses of energy after debridement, and potential perforation of the body cavity or lumen due to the rigidity of the RF electrodes.

The current state of the art would benefit from minimally invasive devices and methods which deliver thermal energy to a desired area or extract energy from a desired area, in a consistent, controlled manner particularly in regions of the body which have variable anatomy.

SUMMARY OF THE INVENTION

An elongate shaft may be introduced through the cervix and into the uterus until the distal opening of the shaft is positioned distal to the internal os and a liner may be deployed either from within the shaft or from an external sheath. The liner may be deployed and allowed to unfurl or unwrap within the uterus allowing a cooling probe to be introduced through the shaft and into the balloon interior. The cooling probe positioned within the liner may be variously configured and may include further variations.

As the cryoablative fluid is introduced into and distributed throughout the catheter lumen, the exhaust catheter may also define one or more openings to allow for the cryoablative fluid to vent or exhaust from the catheter interior and into the interior of the balloon. A coolant reservoir, e.g., nitrous oxide canister, may be fluidly coupled to the handle and/or elongate shaft via a coolant valve which may be optionally controlled by a microcontroller. The coolant reservoir may be in fluid communication with the cooling probe assembly and with the interior of the liner. Additionally, an exhaust lumen in communication with the elongate probe and having a back pressure valve may also include a pressure sensor where one or both of the back pressure sensor and/or valve may also be in communication with the microcontroller.

Further details of the various probes and assemblies which may be used with any of the features described herein are described in the following U.S. patent application Ser. No. 13/361,779 filed Jan. 30, 2012 and Ser. No. 13/900,916 filed May 23, 2013, each of which is incorporated herein by reference in its entirety. Any of the embodiments described herein are intended to be used in any number of combinations with the features of the devices and methods described in these referenced applications.

Because the liner is used to contact the tissue and thermally conduct the heat through the liner, the liner material may be comprised of various materials such as polyurethane, fluorinated ethylene propylene (FEP), polyether ether ketone (PEEK), low density polyethylene, polyethylene terephthalate (PET), polyvinylidene fluoride (PVDF), or any number of other conformable polymers. Moreover, the liner material may have a thickness which remains flexible and strong yet sufficiently thermally conductive, e.g., about 0.0005 to 0.015 in or about 0.001 in. on average. Such a thickness may allow for the liner to remain supple enough to conform desirably to the underlying tissue anatomy and may also provide sufficient clarity for visualizing through the material with, e.g., a hysteroscope.

Once the balloon or liner is initially deployed, it may be expanded by an initial burst of a gas, e.g., air, carbon dioxide, etc., or by the cryogenic fluid. In particular, the tapered portions of the balloon or liner may be expanded to ensure contact with the uterine cornua. The handle assembly may also be used to actuate and control a longitudinal position of the cooling probe relative to the elongate shaft and balloon or liner. The pre-treatment infusion of air as well as the methods for treatment and thawing may be utilized with any of the liner, probe, or apparatus variations described herein. Moreover, the pre-treatment, treatment, or post-treatment procedures may be utilized altogether in a single procedure or different aspects of such procedures may be used in varying combinations depending upon the desired results.

An infusion line may pass from the handle assembly and along or within the sheath and into the interior of the liner. The infusion line may be aligned along the probe such that the infusion line is parallel with a longitudinal axis of the probe and extends towards the distal tip of the probe. Moreover, the infusion line may be positioned along the probe such that the line remains exposed to the corners of the liner which extend towards the cornua. With the infusion line positioned accordingly, the length of the line within the liner may have multiple openings formed along its length which act as delivery ports for the infused cryogenic fluid or gas. A separate translating delivery line, e.g., formed of a Nitinol tube defining an infusion lumen therethrough, may be slidably positioned through the length of the infusion line such that the delivery line may be moved relative to the infusion line which remains stationary relative to the probe.

The openings along the length of the infusion line may be positioned such that the openings are exposed to the sides of the interior of the liner, e.g., cross-drilled. As the cryogenic fluid or gas is introduced through the delivery line, the infused cryogenic fluid or gas may pass through the infusion line and then out through the openings defined along the infusion line. By adjusting the translational position of the delivery line, the delivery line may also cover a selected number of the openings resulting in a number of open delivery ports as well as closed delivery ports which are obstructed by the delivery line position relative to the infusion line.

By translating the delivery line accordingly, the number of open delivery ports and closed delivery ports may be adjusted depending on the desired treatment length and further ensures that only desired regions of the uterine tissue are exposed to the infused cryogenic fluid or gas. Once the number of open delivery ports has been suitably selected, the infused cryogenic fluid or gas may bypass the closed delivery ports obstructed by the delivery line and the fluid or gas may then be forced out through the open delivery ports in a transverse direction as indicated by the infusion spray direction. The terminal end of the infusion line may be obstructed to prevent the distal release of the infused fluid or gas from its distal end. Although in other variations, the terminal end of the infusion line may be left unobstructed and opened.

Turning now to the liner itself, the liner may be formed to have, e.g., a nominal 0.001 in. (or more particularly 0.0012 in. +0.0004/−0.0003) thick flexible membrane such as polyurethane or PELLETHANE® (Lubrizol Advanced Materials, Inc., Cleveland, Ohio). The liner 20 may be optionally formed as a composite from one or more sheets of material, e.g., two sheets of membrane which are RF welded. When laid out in a flattened shape, the liner may shaped in a manner which allows the liner to inflate or expand into a contoured shape which conforms closely to a uterine cavity. The liner itself may be formed to have a uniform thickness over the entire liner. Alternatively, different portions of the liner may also be formed to have differing thicknesses depending upon the desired degree of treatment along differing portions of the liner. For instance, the liner may have varying regions of thickness along proximal portions of the liner relative to distal portions of the liner.

Moreover, to facilitate smooth retraction of the sheath and consistent deployment, the liner may be pleated to fold and collapse in a consistent manner. Because of the thickness of the liner and its suppleness, the liner may conform against the anatomy of the contacted tissue surface. However, the liner may be intentionally sized to be substantially larger than the typical size of the uterine cavity which can average, e.g., about 10 ml for relatively small cavities, about 20 ml for medium sized cavities, and about 50 ml or greater for relatively large size cavities. For instance, the liner may be sized to be, e.g., 1.2 times (or more), greater than the size of the uterine cavity into which the liner is inserted. Because the liner may be sized to be intentionally larger than the uterine cavity to be treated, the liner may never fully expand when deployed within the uterus.

Because liner is constrained from fully expanding within the uterus, folds or portions of the liner may overlap upon itself over the surface of the liner in contact against the surrounding tissue. This is particularly so since the material of the liner may be non-distensible so as to prevent the full deployment of the liner within the uterine cavity. Even with folds or portions of the liner being folded upon itself, the liner may remain sufficiently supple such that the resulting uncontrolled folds allow for complete conformance of the liner against the anatomy of the contacted tissue. Moreover, the thickness of the liner may allow for the heat to be sufficiently conducted from the underlying tissue through, e.g., 1 to 3 layers of the liner, which may result in an overall thickness through the folded liner layers of, e.g., 0.001 to 0.003 in.

While the liner may be oversized to enable the liner to deliberately fold upon or over itself when contacting the underlying tissue, the formation of the folds or portions may occur randomly over the expanded liner. Alternatively, portions of the liner may be optionally pleated or folded such that liner expansion may preferentially cause these pleated or folded sections to fold against the surrounding tissue surface. Having the liner intentionally sized to be larger than the uterine cavity (or any other body lumen) into which the liner is placed may not only ensure that the liner is inhibited from over-expanding, but this also keeps the liner membrane from distending, particularly when frozen, so as to prevent or inhibit the liner from fracturing or ripping during or after treatment.

BRIEF DESCRIPTION OF THE DRAWINGS

FIG. 5A shows the liner in its compacted shape when first deployed or expanded.

FIG. 5B shows an example of the liner having portions folded upon itself when expanded into full conformance within the uterus.

FIG. 5C shows an example of the liner when fully expanded to its maximum configuration outside of the uterus.

FIG. 5D shows a partial cross-sectional end view of the liner folded upon itself when expanded into contact against the tissue surface.

DETAILED DESCRIPTION OF THE INVENTION

In treating an expandable and/or variably sized body lumen such as the uterus, a device generally having a cooling probe and a reconfigurable liner may be advanced within the body lumen and expanded into contact against the interior tissue surface. The liner may be configured to conform against the interior tissue surface and to resist rupture at low and high temperatures. For example, the liner when expanded may have a shape which approximates the body lumen in which it is inflated and/or come in various sizes to accommodate different patient anatomies. The liner may be formed to taper and have two rounded portions for expanding into intimate contact at the uterine cornu without painful deformation or distention of the uterus at a pressure, e.g., less than 150 mmHg.

Moreover, the liner may have a wall which is relatively thin (e.g., 0.040 in. or less) to facilitate thermal conduction through the liner material. The liner may also be sufficiently thin such that folding of the liner on itself does not create a significant thermal barrier allowing for an even ablation in the event that a non-compliant liner is used. Generally, once the elongate shaft has been introduced through the cervix and into the uterus, the distal opening of the shaft may be positioned distal to the internal os and the liner may be deployed either from within the shaft or from an external sheath (described below in further detail). The liner may be deployed and allowed to unfurl or unwrap within the uterus. A cooling probe may be introduced through the shaft and into the liner interior.

Further details of the various probes and assemblies which may be used with any of the features described herein are described in the following U.S. patent application Ser.

No. 13/361,779 filed Jan. 30, 2012 and Ser. No. 13/900,916 filed May 23, 2013, each of which is incorporated herein by reference in its entirety. Any of the embodiments described herein are intended to be used in any number of combinations with the features of the devices and methods described in these referenced applications.

Because the liner is used to contact the tissue and thermally conduct the heat through the liner, the liner material may be comprised of various materials such as polyurethane, fluorinated ethylene propylene (FEP), polyether ether ketone (PEEK), low density polyethylene, polyethylene terephthalate (PET), polyvinylidene fluoride (PVDF), or any number of other conformable polymers. Moreover, the liner material may have a thickness which remains flexible and strong yet sufficiently thermally conductive, e.g., about 0.0005 to 0.015 in. or about 0.001 in. on average. Such a thickness may allow for the liner to remain supple enough to conform desirably to the underlying tissue anatomy and may also provide sufficient clarity for visualizing through the material with, e.g., a hysteroscope.

Figure 1A:
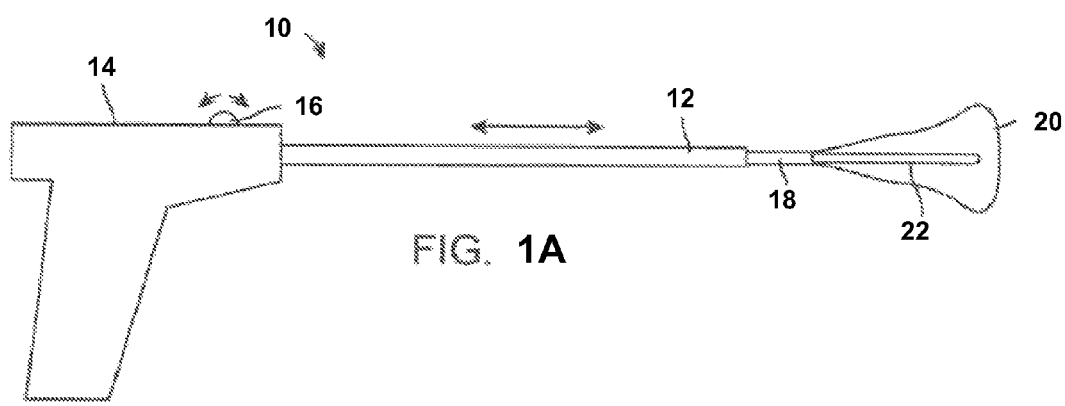
FIG. 1A shows a side view of an integrated treatment assembly.

The cooling probe 22 as well as the balloon assembly may be variously configured, for instance, in an integrated treatment assembly 10 as shown in the side view of FIG. 1A. In this variation, the assembly 10 may integrated the elongate shaft 18 having the balloon or liner 20 extending therefrom with the cooling probe 22 positioned translatably within the shaft 18 and balloon or liner 20. A separate translatable sheath 12 may be positioned over the elongate shaft 18 and both the elongate shaft 18 and sheath 12 may be attached to a handle assembly 14. The handle assembly 14 may further comprise an actuator 16 for controlling a translation of the sheath 12 for balloon or liner 20 delivery and deployment. The sheath 12 may be configured to have a diameter of, e.g., 5.5 mm or less, to prevent the need for dilating the cervix.

Figure 1B:
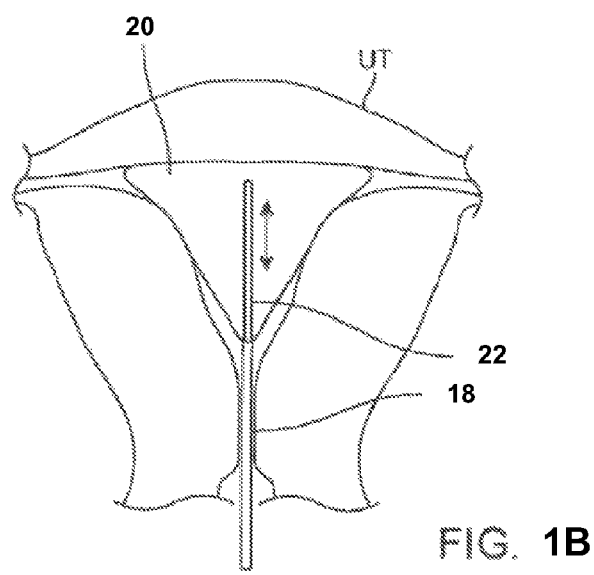
FIG. 1B shows an example of the assembly advanced through the cervix and into the uterus where the sheath may be retracted via the handle assembly to deploy the balloon.

With the sheath 12 positioned over the elongate shaft 18 and balloon or liner 20, the assembly 10 may be advanced through the cervix and into the uterus UT where the sheath 12 may be retracted via the handle assembly 14 to deploy the balloon or liner 20, as shown in FIG. 1B. As described above, once the balloon or liner 20 is initially deployed from the sheath 12, it may be expanded by an initial burst of a gas, e.g., air, carbon dioxide, etc., or by the cryogenic fluid. In particular, the tapered portions of the balloon or liner 20 may be expanded to ensure contact with the uterine cornu. The handle assembly 14 may also be used to actuate and control a longitudinal position of the cooling probe 22 relative to the elongate shaft 18 and balloon or liner 20 as indicated by the arrows.

Figure 1C:
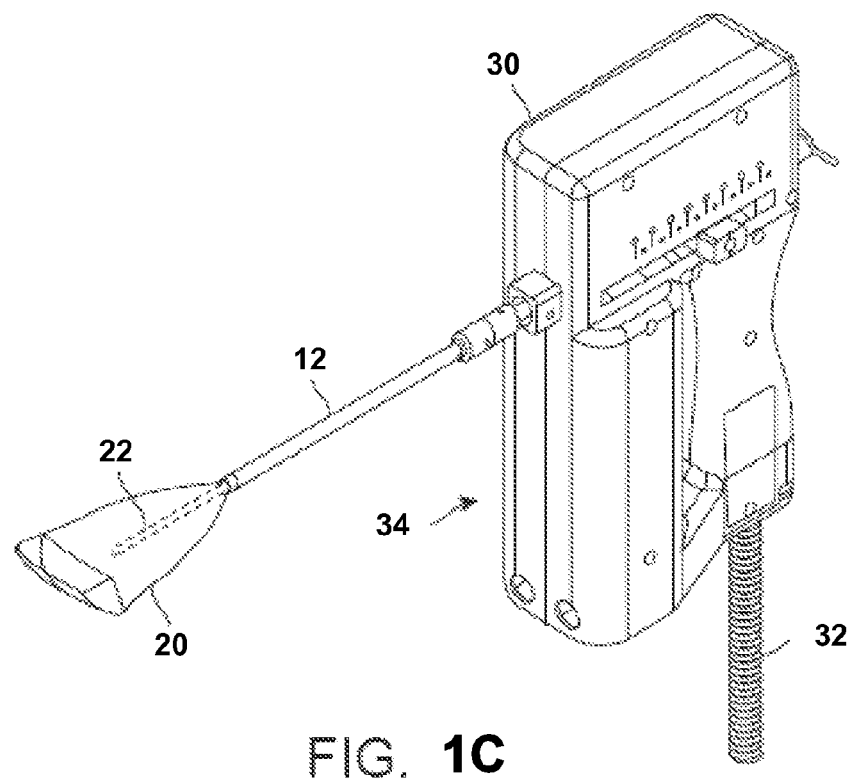
FIG. 1C shows a perspective view of a cryoablation assembly having a handle assembly which may integrate the electronics and pump assembly within the handle itself.

In another variation of the treatment assembly, FIG. 1C shows a perspective view of a cryoablation assembly having a handle assembly 30 which may integrate the electronics and pump assembly 34 within the handle itself. An exhaust tube 32 may also be seen attached to the handle assembly 30 for evacuating exhausted or excess cryoablative fluid or gas from the liner 20. Any of the cryogenic fluids or gases described herein may be utilized, e.g., compressed liquid-to-gas phase change of a compressed gas such as nitrous oxide ($N_2O$), carbon dioxide ($CO_2$), Argon, etc. The cooling probe 22 may be seen extending from sheath 12 while surrounded or enclosed by the balloon or liner 20. Hence, the handle assembly 30 with coupled cooling probe 22 and liner 20 may provide for a single device which may provide for pre-treatment puff-up or inflation of the liner 20, active cryoablation treatment, and/or post-treatment thaw cycles.

The handle assembly 30 may also optionally incorporate a display for providing any number of indicators and/or alerts to the user. For instance, an LCD display may be provided on the handle assembly 30 (or to a separate control unit connected to the handle assembly 30) where the display counts down the treatment time in seconds as the ablation is occurring. The display may also be used to provide measured pressure or temperature readings as well as any number of other indicators, symbols, or text, etc., for alerts, instructions, or other indications. Moreover, the display may be configured to have multiple color-coded outputs, e.g., green, yellow, and red. When the assembly is working through the ideal use case, the LED may be displayed as a solid green color. When the device requires user input (e.g. when paused and needing the user to press the button to re-start treatment) the LED may flash or display yellow. Additionally, when the device has faulted and treatment is stopped, the LED may flash or display a solid red color.

Figure 1D:
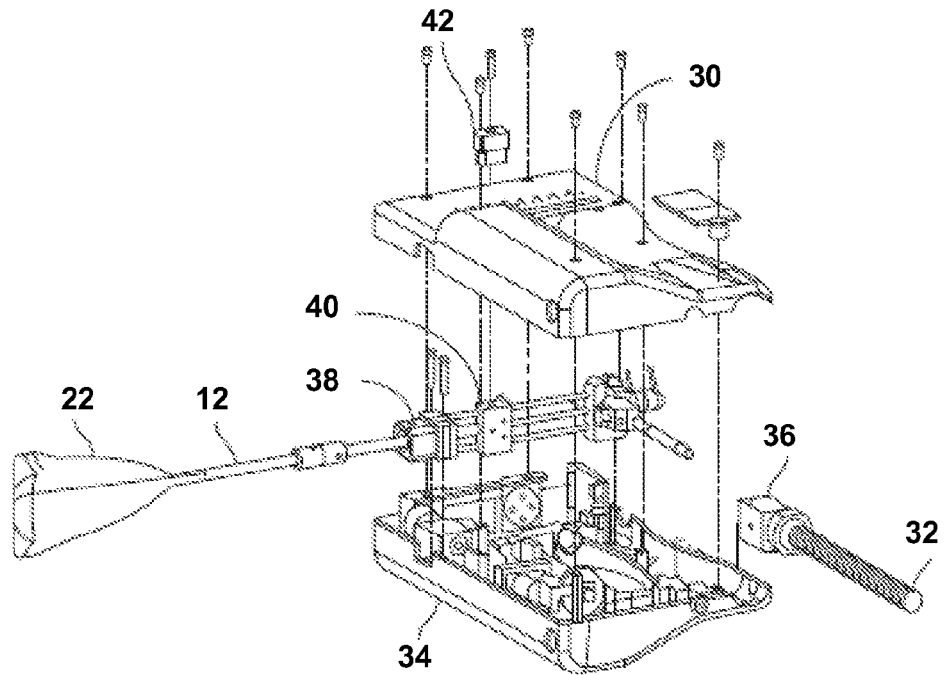
FIG. 1D shows the handle assembly in a perspective exploded view illustrating some of the components which may be integrated within the handle.

FIG. 1D shows the handle assembly 30 in a perspective exploded view to illustrate some of the components which may be integrated within the handle 30. As shown, the liner 20 and sheath 12 may be coupled to a sheath bearing assembly 38 and slider base block assembly 40 for controlling the amount of exposed treatment length along the cooling probe 22 (and as described in further detail below). An actuatable sheath control 42 may be attached to the slider base block assembly 40 for manually controlling the treatment length of the cooling probe 22 as well. Along with the electronics and pump assembly 34 (which may optionally incorporate a programmable processor or controller in electrical communication with any of the mechanisms within the handle 30), an exhaust valve 36 (e.g., actuated via a solenoid) may be coupled to the exhaust line 32 for controlling not only the outflow of the exhausted cryoablation fluid or gas but also for creating or increasing a backpressure during treatment, as described in further detail below.

Alternatively, an active system may be integrated into the handle or coupled to the handle 30 where a heat sink may be connected to a temperature sensor and electrical circuit which is controlled by a processor or microcontroller. The heat sink may promote heat transfer and causes any liquid exhaust to evaporate. When the temperature of the heat sink reaches the boiling temperature of, e.g., nitrous oxide (around −89° C.), the handle may be configured to slow or stop the delivery of the cryogenic fluid or gas to the uterine cavity.

The pre-treatment infusion of air as well as the methods for treatment and thawing may be utilized with any of the liner, probe, or apparatus variations described herein. Moreover, the pre-treatment, treatment, or post-treatment procedures may be utilized altogether in a single procedure or different aspects of such procedures may be used in varying combinations depending upon the desired results.

Additionally and/or optionally, the handle 30 may incorporate an orientation sensor to facilitate maintaining the handle 30 in a desirable orientation for treatment. One variation may incorporate a ball having a specific weight covering the exhaust line 32 such that when the handle 30 is held in the desirable upright orientation, the treatment may proceed uninterrupted. However, if the handle 30 moved out of its desired orientation, the ball may be configured to roll out of position and trigger a visual and/or auditory alarm to alert the user. In another variation, an electronic gyroscopic sensor may be used to maintain the handle 30 in the desired orientation for treatment.

Figure 2A:
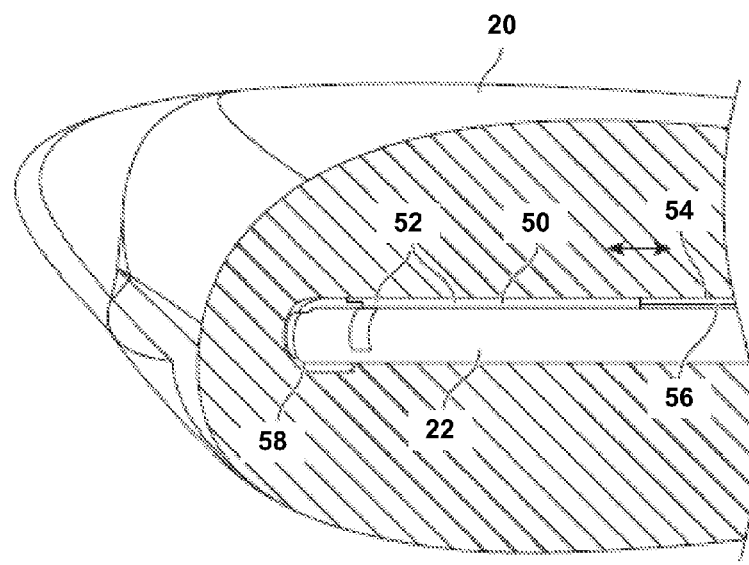
FIGS. 2A and 2B show cross-sectional side views of yet another variation of a cooling probe which utilizes a single infusion line in combination with a translatable delivery line.
Figure 2B:
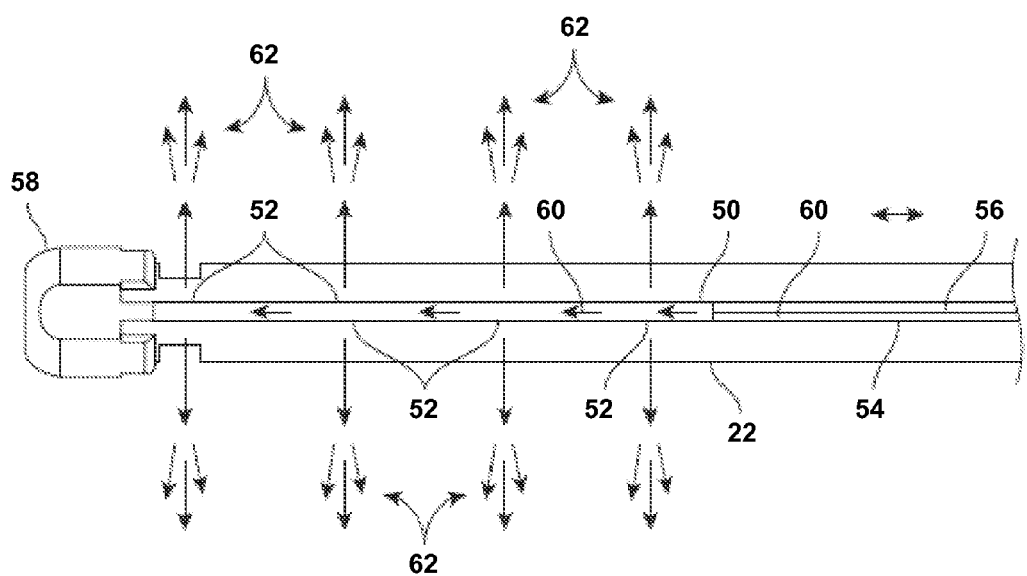

FIGS. 2A and 2B show cross-sectional side views of yet another variation of a cooling probe which utilizes a single infusion line in combination with a translatable delivery line. To accommodate various sizes and shapes of uterine cavities, the cooling probe may have a sliding adjustment that may be set, e.g., according to the measured length of the patient's uterine cavity. The adjustment may move along the sheath along the exhaust tube as well as the delivery line within the infusion line. The sheath may constrain the liner 20 and also control its deployment within the cavity.

In this variation, an infusion line 50 (as described above) may pass from the handle assembly and along or within the sheath and into the interior of liner 20. The infusion line 50 may be aligned along the probe 22 such that the infusion line 50 is parallel with a longitudinal axis of the probe 22 and extends towards the distal tip 58 of the probe 22. Moreover, the infusion line 50 may be positioned along the probe 22 such that the line 50 remains exposed to the corners of the liner 20 which extend towards the cornua. With the infusion line 50 positioned accordingly, the length of the line 50 within the liner 20 may have multiple openings formed along its length which act as delivery ports for the infused cryogenic fluid or gas. A separate translating delivery line 56, e.g., formed of a Nitinol tube defining an infusion lumen therethrough, may be slidably positioned through the length of the infusion line 50 such that the delivery line 56 may be moved (as indicated by the arrows in FIG. 2A) relative to the infusion line 50 which remains stationary relative to the probe 22.

The openings along the length of the infusion line 50 may be positioned such that the openings are exposed to the sides of the interior of the liner 20, e.g., cross-drilled. As the cryogenic fluid or gas is introduced through the delivery line 56, the infused cryogenic fluid or gas 60 may pass through the infusion line 50 and then out through the openings defined along the infusion line 50. By adjusting the translational position of the delivery line 56, the delivery line 56 may also cover a selected number of the openings resulting in a number of open delivery ports 52 as well as closed delivery ports 54 which are obstructed by the delivery line 56 position relative to the infusion line 50, as shown in the top view of FIG. 2B.

By translating the delivery line 56 accordingly, the number of open delivery ports 52 and closed delivery ports 54 may be adjusted depending on the desired treatment length and further ensures that only desired regions of the uterine tissue are exposed to the infused cryogenic fluid or gas 60. Once the number of open delivery ports 52 has been suitably selected, the infused cryogenic fluid or gas 60 may bypass the closed delivery ports 54 obstructed by the delivery line 56 and the fluid or gas may then be forced out through the open delivery ports 52 in a transverse direction as indicated by the infusion spray direction 62. The terminal end of the infusion line 50 may be obstructed to prevent the distal release of the infused fluid or gas 60 from its distal end. Although in other variations, the terminal end of the infusion line 50 may be left unobstructed and opened.

Figure 3A:
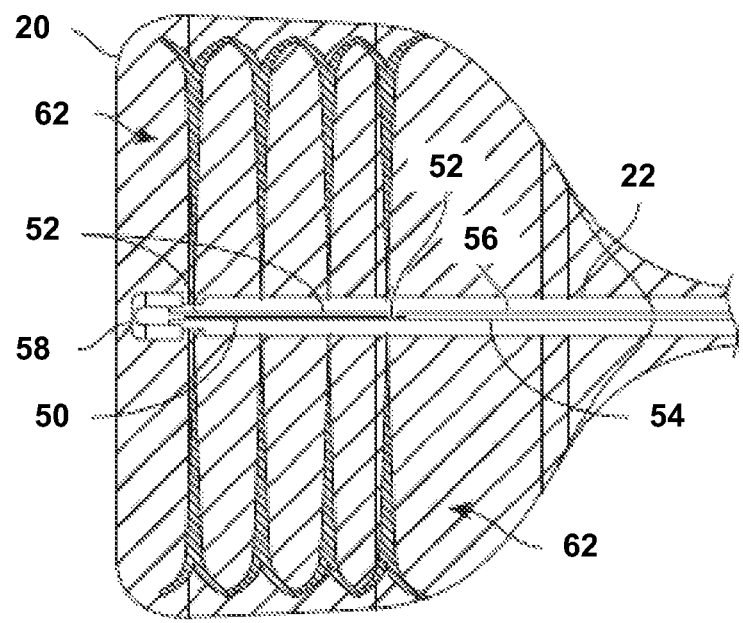
FIGS. 3A and 3B show top and perspective views of the expanded liner with four pairs of the open delivery ports exposed in apposed direction.
Figure 3B:
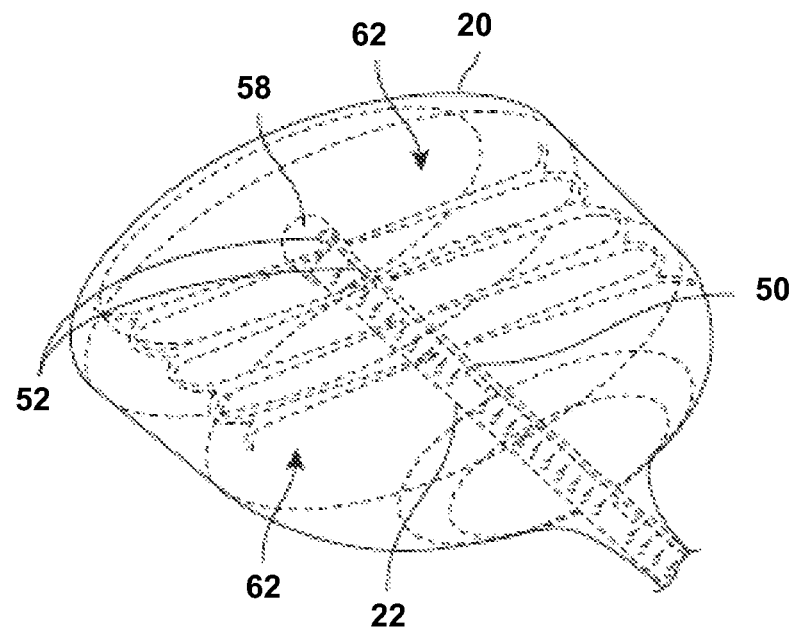

FIGS. 3A and 3B show top and perspective views of the expanded liner 20 with four pairs of the open delivery ports 52 exposed in apposed direction. Because the infused fluid or gas 60 may be injected into the liner 20, e.g., as a liquid, under relatively high pressure, the injected cryogenic liquid may be sprayed through the open delivery ports 52 in a transverse or perpendicular direction relative to the cooling probe 22. The laterally infused cryogenic fluid 62 may spray against the interior of the liner 20 (which is contacted against the surrounding tissue surface) such that the cryogenic liquid 62 coats the interior walls of the liner 20 due to turbulent flow causing heavy mixing. As the cryogenic liquid 62 coats the liner surface, the sprayed liquid 62 may absorb heat from the tissue walls causing rapid cooling of the tissue while also evaporating the liquid cryogen to a gas form that flows out through the cooling probe 22. This rapid cooling and evaporation of the cryogenic liquid 62 facilitates the creation of a fast and deep ablation over the tissue. During treatment, the temperature within the cavity typically drops, e.g., −89° C., within 6-7 seconds after the procedure has started. While the interior walls of the liner 20 are first coated with the cryogenic liquid 62, the cryogenic liquid 62 may no longer change phase as the procedure progresses.

Figure 4A:
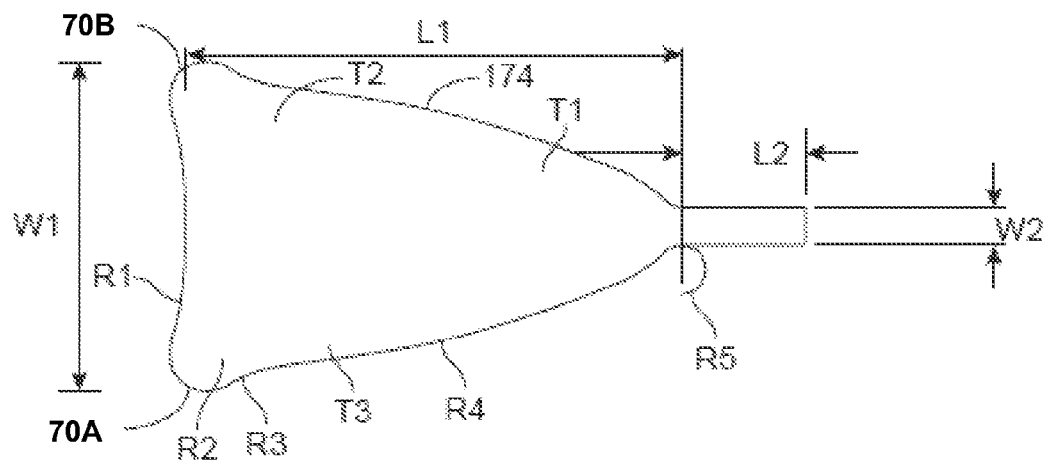
FIGS. 4A and 4B show top and perspective views of a liner illustrating its curved features when flattened and expanded and then deployed in a consistent manner.
Figure 4B:
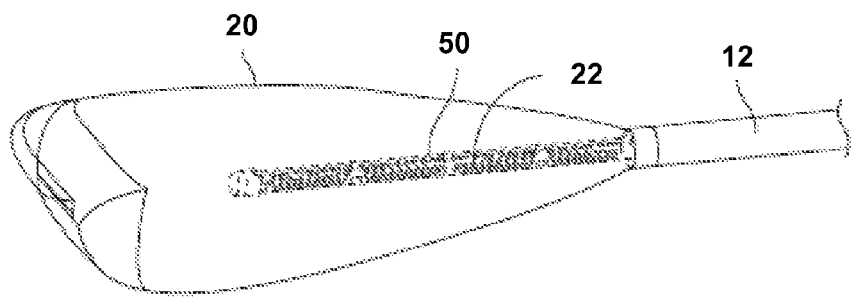

Turning now to the liner itself, the liner may be formed to have, e.g., a nominal 0.001 in. (or more particularly 0.0012 in. +0.0004/−0.0003) thick flexible membrane such as polyurethane or PELLETHANE® (Lubrizol Advanced Materials, Inc., Cleveland, Ohio). The liner 20 may be optionally formed as a composite from one or more sheets of material, e.g., two sheets of membrane which are RF welded. When laid out in a flattened shape, the liner 20 may shaped in a manner, as shown in the top view of FIG. 4A, which allows the liner 20 to inflate or expand into a contoured shape which conforms closely to a uterine cavity, as shown in the perspective view of FIG. 4B. FIG. 4A shows one example of a flattened liner 20 which gently tapers from the opening to a curved shape forming a first curved portion 70A and a second curved portion 70B opposite to the first curved portion 70A. The liner 20 may hence taper gently from a first width W1, e.g., about 2.4 in., down to a second width W2, e.g., about 0.3 in., over a length L1 of, e.g., about 3.5 in. The neck may form a length L2, e.g., about 0.9 in.

The region between each of the first and second curved portions 70A, 70B may also be curved to have a radius R1 of, e.g., about 3.5 in., while curved portions 70A, 70B may also be curved to each have a radius R2 of, e.g., about 0.3 in. The portion of the liner proximal to the portions 70A, 70B may also have a radius R3, e.g., about 1.1 in., and an oppositely radiused portion of radius R4, e.g., about 8.0 in. The region between the liner 20 and neck may further have a radius R5, e.g., about 0.2 in.

The liner 20 itself may be formed to have a uniform thickness over the entire liner. Alternatively, different portions of the liner 20 may also be formed to have differing thicknesses depending upon the desired degree of treatment along differing portions of the liner 20. For instance, the liner 20 may have varying regions of thickness T1, T2, T3 along proximal portions of the liner relative to distal portions of the liner.

Figure 4C:
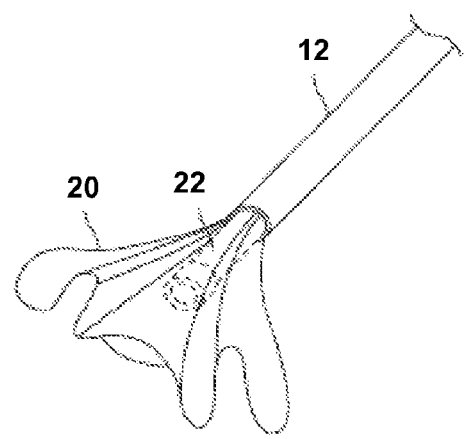
FIG. 4C shows a perspective view of a liner which may be pleated to fold and collapse in a consistent manner.

Moreover, to facilitate smooth retraction of the sheath and consistent deployment, the liner 20 may be pleated to fold and collapse in a consistent manner, as shown in the perspective view of FIG. 4C. The liner 20 may be pleated, e.g., using a fixture during manufacturing.

Because of the thickness of the liner 20 and its suppleness, the liner 20 may conform against the anatomy of the contacted tissue surface. However, the liner 20 may be intentionally sized to be substantially larger than the typical size of the uterine cavity which can average, e.g., about 10 ml for relatively small cavities, about 20 ml for medium sized cavities, and about 50 ml or greater for relatively large size cavities. For instance, the liner 20 may be sized to be, e.g., 1.2 times (or more), greater than the size of the uterine cavity into which the liner 20 is to be inserted. Because the liner 20 may be sized to be intentionally larger than the uterine cavity to be treated, the liner 20 may never fully expand when deployed within the uterus UT. An example is illustrated in the side views of FIGS. 5A to 5C. FIG. 5A shows the liner 20' in its compacted shape when first deployed or expanded. FIG. 5B shows an example of the liner 20" when expanded into full conformance within the uterus UT and FIG. 5C shows an example of the liner 20'"

when fully expanded to its maximum configuration outside of the uterus UT. The profile of liner 20''' is provided for comparison against the constrained expansion of the liner 20" within the uterus UT.

Because liner 20" is constrained from fully expanding within the uterus UT, as shown in FIG. 5B, folds or portions 80 of the liner 20" may overlap upon itself over the surface of the liner in contact against the surrounding tissue. This is particularly so since the material of the liner 20" may be non-distensible so as to prevent the full deployment of the liner 20" within the uterine cavity UT.

In other variations, the liner may be optionally distensible so that the liner is able to be stretched to accommodate a body lumen which may be larger than the liner. For instance, the liner may have an internal volume of, e.g., 40 ml, when the liner is expanded but un-distended or un-stretched. For body lumens having a volume greater than 40 ml, the liner may be optionally expanded until stretched to, e.g., about 400 ml when pressurized to less than 20 mmHg, to ensure contact with the tissue surfaces before the liner ruptures. Even with such a distensible liner, the liner may still have folds or portions 80 which may overlap upon itself over the surface of the liner in contact with the surrounding tissue without having any appreciable effect on the thermal heat transfer across the folds.

Even with folds or portions 80 of the liner being folded upon itself, the liner 20" may remain sufficiently supple such that the resulting uncontrolled folds allow for complete conformance of the liner 20" against the anatomy of the contacted tissue, as shown in the partial cross-sectional end view of FIG. 5D. Moreover, the thickness of the liner 20" may allow for the heat to be sufficiently conducted from the underlying tissue through, e.g., 1 to 3 layers of the liner, which may result in an overall thickness through the folded liner layers of, e.g., 0.001 to 0.003 inches.

While the liner 20 may be oversized to enable the liner 20 to deliberately fold upon or over itself when contacting the underlying tissue, the formation of the folds or portions 80 may occur randomly over the expanded liner. Alternatively, portions of the liner 20 may be optionally pleated or folded such that liner expansion may preferentially cause these pleated or folded sections to fold against the surrounding tissue surface. Having the liner intentionally sized to be larger than the uterine cavity UT (or any other body lumen) into which the liner is placed may not only ensure that the liner is inhibited from over-expanding, but this also keeps the liner membrane from distending, particularly when frozen, so as to prevent or inhibit the liner 20 from fracturing or ripping during or after treatment.

While illustrative examples are described above, it will be apparent to one skilled in the art that various changes and modifications may be made therein. Moreover, various apparatus or procedures described above are also intended to be utilized in combination with one another, as practicable. The appended claims are intended to cover all such changes and modifications that fall within the true spirit and scope of the invention.

What is claimed is:

1. A tissue treatment system, comprising:
   an elongate probe having a distal tip and a flexible length;
   at least one infusion lumen positioned through or along the elongate probe, wherein the infusion lumen defines one or more openings along its length;
   at least one delivery lumen slidingly positioned through or along the infusion lumen wherein translation of the delivery lumen relative to the infusion lumen controls a number of unobstructed openings along the infusion lumen such that proximal translational of the delivery lumen relative to the infusion lumen from a first location increases the number of unobstructed openings, and distal translation of the delivery lumen relative to the infusion lumen from the first location decreases the number of unobstructed openings; and
   a liner configured to have pre-formed folds or pleats and enclosing the probe, where the liner is expandable from a delivery configuration which is folded and collapsed within a sheath to an expanded configuration which is sized to be larger than a uterine cavity of an adult human to be treated,
   wherein the liner defines a suppleness such that expansion of the liner within the uterine cavity causes portions of the liner to fold upon itself in a controlled manner against a tissue surface of the uterine cavity while conforming against the tissue surface, and
   wherein the liner is formed of two sheets of membrane which are welded to one another to form a flattened shape in which the liner tapers and in its expanded configuration forms a contoured shape.

2. The system of claim 1 wherein the portions are folded to form between 1 to 3 layers of the liner.

3. The system of claim 1 wherein the portions are folded to a thickness of between 0.001 to 0.003 in of the liner.

4. The system of claim 1 wherein the delivery lumen comprises a Nitinol delivery tube slidingly positioned through the infusion lumen.

5. The system of claim 1 further comprising a reservoir of a cryoablative fluid in fluid communication with the delivery lumen.

6. The system of claim 5 wherein the cryoablative fluid comprises nitrous oxide or argon.

* * * * *